United States Patent
Yanagawa et al.

(10) Patent No.: US 6,500,951 B1
(45) Date of Patent: Dec. 31, 2002

(54) PROCESS FOR PREPARING PYRIDAZIN-3-ON DERIVATIVES

(75) Inventors: Masao Yanagawa, Ibaraki (JP); Masahiko Mizuno, Suita (JP); Yoshiaki Oda, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/857,033

(22) PCT Filed: Dec. 7, 1999

(86) PCT No.: PCT/JP99/06842
§ 371 (c)(1),
(2), (4) Date: Jun. 20, 2001

(87) PCT Pub. No.: WO00/34249
PCT Pub. Date: Jun. 15, 2000

(30) Foreign Application Priority Data

Dec. 9, 1998 (JP) ............... 10-350274
Jun. 18, 1999 (JP) ............... 11-172464

(51) Int. Cl.⁷ ............... C07D 237/14
(52) U.S. Cl. ............... 544/239; 562/440
(58) Field of Search ............... 544/239

(56) References Cited

FOREIGN PATENT DOCUMENTS

| DE | 19754348 | 6/1998 |
|---|---|---|
| WO | 9817632 A | 4/1998 |
| WO | 9817633 A | 4/1998 |
| WO | 9952878 A | 10/1999 |

*Primary Examiner*—Emily Bernhardt
(74) *Attorney, Agent, or Firm*—Birch, Stewart, Kolasch & Birch, LLP

(57) ABSTRACT

A pyridazin-3-on derivative of the formula (1):

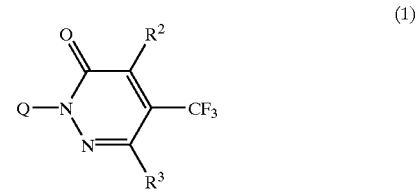

in which $R^2$ is a hydrogen atom or a $C_1$–$C_3$ alkyl group, $R^3$ is a hydrogen atom or a $C_1$–$C_3$ alkyl group, and Q is an optionally substituted phenyl group can be prepared at a high yield and high purity by ring closing a carboxylic acid derivative of the formula (2):

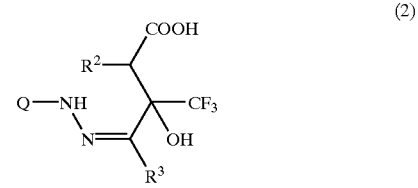

in which $R^2$, $R^3$ and Q are the same as defined above, or its salt in the presence of a nitrogen-containing aromatic compound and a boron compound.

18 Claims, No Drawings

PROCESS FOR PREPARING PYRIDAZIN-3-ON DERIVATIVES

This application is the national phase under 35 U.S.C. § 371 of PCT, International Application Ser. No. PCT/JP99/06842 which has an International filing date of Dec. 7, 1999, which designated the United States of America and was published in English.

FIELD OF THE INVENTION

The present invention relates to a process for preparing pyridazin-3-on derivatives.

BACKGROUND ART

WO97/7104 discloses that pyridazin-3-on derivatives have good herbicidal activities, and WO98/17632 discloses that carboxylic acids derivatives and their salts are useful intermediates for the preparation of pyridazin-3-on derivatives, and a process for preparing pyridazin-3-on derivatives from such intermediates. For example, WO98/17632 discloses a process of reacting a lower carboxylic acid and a base with such an intermediate.

However, the disclosed process does not always produce a desired product at an industrially satisfactory yield and purity.

SUMMARY OF THE INVENTION

One object of the. present invention is to provide a process for preparing pyridazin-3-on derivatives from carboxylic acid derivatives or their salts advantageously in an industrial scale.

This and other objects are accomplished by a method for preparing a pyridazin-3-on derivative of the formula (1):

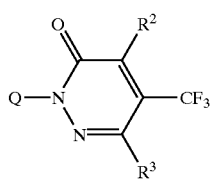

(1)

wherein $R^2$ is a hydrogen atom or a $C_1$–$C_3$ alkyl group, $R^3$ is a hydrogen atom or a $C_1$–$C_3$ alkyl group, and Q is a phenyl group which may optionally be substituted, comprising the step of ring closing a carboxylic acid derivative of the formula (2):

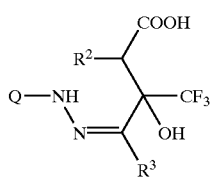

(2)

wherein $R^2$, $R^3$ and Q are the same as defined above, or its salt in the presence of a nitrogen-containing aromatic compound and a boron compound.

DETAILED DESCRIPTION OF THE INVENTION

The carboxylic acid of the formula (2) or its salt, which is a raw material used; in the process of the present invention, will be explained.

In the carboxylic acid of the formula (2) or its salt, examples of a substituent which may optionally present on the phenyl group Q include halogen atoms, and a group of the formula: —$ZR^1$ in which Z is an oxygen atom or a sulfur atom, and $R^1$ is a hydrogen atom, a $C_1$–$C_6$ alkyl group, a $C_1$–$C_6$ haloalkyl group, a $C_3$–$C_8$ cycloalkyl group, a benzyl group, a $C_3$–$C_6$ alkenyl group, a $C_3$–$C_6$ haloalkenyl group, a $C_3$–$C_6$ alkynyl group, a $C_3$–$C_6$ haloalkynyl group, a cyano-$C_1$–$C_6$ alkyl group, a $C_2$–$C_8$ (alkoxyalkyl) group, a $C_2$–$C$, (alkoxythioalkyl) group, a carboxy-$C_1$–$C_6$ alkyl group, ($C_1$–$C_8$ alkoxy) carbonyl-$C_1$–$C_6$ alkyl group, [($C_1$–$C_4$ alkoxy)-$C_1$–$C_4$ alkoxy]carbonyl-$C_1$–$C_6$ alkyl group, a ($C_3$–$C_8$ cycloalkoxy)carbonyl-$C_1$–$C_6$ alkyl group or a [($C_1$–$C_6$ alkoxy)carbonyl-$C_1$–$C_6$ alkyl]oxycarbonyl-$C_1$–$C_6$ alkyl group, wherein the positions and number of the substituents are arbitrary.

Preferably, the group Q is an optionally substituted phenyl group of the formula (3):

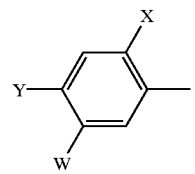

(3)

wherein X is a hydrogen atom or a halogen atom, Y is a halogen atom, and W is a hydrogen atom or a group of the formula: —$ZR^1$ in which Z and $R^1$ are the same as defined above.

Examples of the halogen atom for X and Y include a fluorine atom, a chlorine atom, a bromine atom, etc.

Examples of the $C_1$–$C_6$ alkyl group for $R^1$ include a methyl group, an ethyl group, a propyl group, an isopropyl group, a butyl group, an isobutyl group, a tert.-butyl group, an amyl group, an isoamyl group, a tert.-amyl group, etc.

Examples of the $C_1$–$C_6$ haloalkyl group include a 2-chloroethyl group, a 2-bromoethyl group, a 2,2,2-trifluoroethyl group, etc.

Examples of the $C_3$–$C_8$ cycloalkyl group include a cyclopropyl group, a cyclobutyl group, a cyclopentyl group, a cyclohexyl group, etc.

Examples of the $C_3$–$C_6$ alkenyl group include an allyl group, a 1-methyl-2-propenyl group, a 3-butenyl group, a 2-butenyl group, a 3-methyl-2-butenyl group, a 2-methyl-3-butenyl group, etc.

Examples of the $C_3$–$C_6$ haloalkenyl group include a 2-chloro-2-propenyl group, a 3,3-dichloro-2-propenyl group, etc.

Examples of the $C_3$–$C_6$ alkynyl group include a propargyl group, a 1-methyl-2-propynyl group, a 2-butynyl group, a 1,1-dimethyl-2-propynyl group, etc.

Examples of the $C_3$–$C_6$ haloalkynyl group include 3-bromopropargyl group, etc.

Examples of the cyano-$C_1$–$C_6$ alkyl group include a cyanomethyl group, etc.

Examples of the $C_2$–$C_8$ alkoxyalkyl group include a methoxymethyl group, a methoxyethyl group, an ethoxymethyl group, an ethoxyethyl group, etc.

Examples of the $C_2$–$C_8$ alkylthioalkyl group include a methylthiomethyl group, a methylthioethyl group, etc.

Examples of the carboxy-$C_1$–$C_6$ alkyl group include a carboxymethyl group, a 1-carboxyethyl group, a 2-carboxyethyl group, etc.

Examples of the ($C_1$–$C_8$ alkoxy)carbonyl-$C_1$–$C_6$ alkyl group include a methoxycarbonylmethyl group, an ethoxycarbonylmethyl group, a propoxycarbonylmethyl group, an isopropoxycarbonylmethyl group, a butoxycarbony.methyl group, an isobutoxycarbonylmethyl group, a tert.-butoxycarbonylmethyl group, an amyloxycarbonylmethyl group, an isoamyloxycarbonylmethyl group, a tert.-amyloxy-carbonylmethyl group, a 1-methoxycarbonylethyl group, a 1-ethoxycarbonylethyl group, a 1-propoxycarbonylethyl group, a 1-isopropoxycarbonylethyl group, a 1-butoxycarbonylethyl group, a 1-isobutoxycarbonylethyl group, a 1-tert.-butoxycarbonylethyl group, a 1-amyloxycarbonylethyl group, a 1-isoamyloxycarbony-ethyl group, a 1-tert.-amyloxycarbonylethyl group, etc.

Examples of the [($C_1$–$C_4$ alkoxy)-$C_1$–$C_4$ alkoxy]carbonyl-$C_1$–$C_6$ alkyl group include a methoxymethoxycarbonylmethyl group, a methoxyethoxycarbonylmethyl group, a 1-methoxyethoxycarbonylethyl group, etc.

Examples of the ($C_3$–$C_8$ cycloalkoxy)carbonyl-$C_1$–$C_6$ alkyl group include a cyclobutyloxycarbonylmethyl group, a cyclopentyloxycarbonylmethyl group, a cyclohexyloxycarbonyl-methyl group, a 1-cyclobutyloxycarbonylethyl group, a 1-cyclopentyloxycarbonylethyl group, a 1-cyclohexyloxycarbonylethyl group, etc.

Examples of the [($C_1$–$C_6$ alkoxy)carbonyl-$C_1$–$C_6$ alkyl]oxy-carbonyl-$C_1$–$C_6$ alkyl group include a (methoxycarbonyl)methoxycarbonylmethyl group, an (ethoxycarbonyl)methoxycarbonylmethyl group, etc.

Examples of the $C_1$–$C_3$ alkyl group for $R^2$ and $R^3$ include a methyl group, an ethyl group, a propyl group, etc.

The salts of the carboxylic acid derivative of the formula (2) may be the salts of the above exemplified carboxylic acids and organic bases. Examples of such organic bases include nitrogen-containing aromatic compounds (e.g. pyridine, 4-dimethylaminopyridine, 2-picoline, 3-picoline, 4-picoline, 5-ethyl-2-methylpyridine, etc.), dialkylaniline derivatives (e.g. N,N-dimethylaniline, N,N-diethylaniline, etc.), tertiary amines (e.g. triethylamine, diisopropylethylamine, tri-n-propylamine, tri-n-butylamine, etc.), and the like.

Hereinafter, the specific carboxylic acid derivatives of the formula (2) as the raw materials are exemplified:

| Compound No. | Carboxylic acid derivative |
|---|---|
| 2-10 | (structure: 4-Cl, 2-F, 5-O-propargyl phenyl-NH-N=CH-C(CH₃)(CF₃)(OH)-COOH... shown as aryl-NH-N=CH-C(CF₃)(OH)-CH(CH₃)-COOH) |
| 2-11 | (structure: 4-Cl, 2-F, 5-S-propargyl phenyl-NH-N=CH-C(CF₃)(OH)-CH(CH₃)-COOH) |
| 2-12 | (structure: 2,4-diCl, 5-O-iPr phenyl-NH-N=CH-C(CF₃)(OH)-CH₂-COOH) |
| 2-13 | (structure: 2,4-diCl, 5-OCH₃ phenyl-NH-N=CH-C(CF₃)(OH)-CH₂-COOH) |
| 2-14 | (structure: 2,4-diCl, 5-OCH₂CH₃ phenyl-NH-N=CH-C(CF₃)(OH)-CH₂-COOH) |
| 2-15 | (structure: 2,4-diCl, 5-O-iPr phenyl-NH-N=CH-C(CF₃)(OH)-CH(Et)-COOH) |
| 2-16 | (structure: 2,4-diCl, 5-OCH₃ phenyl-NH-N=CH-C(CF₃)(OH)-CH(Et)-COOH) |
| 2-17 | (structure: 2,4-diCl, 5-OCH₂CH₃ phenyl-NH-N=CH-C(CF₃)(OH)-CH(Et)-COOH) |
| 2-18 | (structure: 4-Cl-phenyl-NH-N=CH-C(CF₃)(OH)-CH₂-COOH) |

However, the raw materials that can be used in the present invention are not limited thereto.

Examples of the a boron compound to be used in the process of the present invention are as follows:

$$R^4\!-\!\!\overset{\overset{\displaystyle R^5}{|}}{B}\!-\!R^6 \qquad (4)$$

wherein $R^4$, $R^1$ and $R^6$ are the same and different and represent a hydroxyl group, a $C_1$–$C_6$ alkyl group, a $C_1$–$C_6$ alkoxy group, a phenyl group which may optionally be substituted with at least one substituent (e.g. a halogen atom, a $C_1$–$C_4$ alkyl group, a $C_1$–$C_3$ haloalkyl group, a $C_1$–$C_3$ alkoxy group, a nitro group, an amino group, a carboxyl group, a $C_1$–$C_3$ amide group, a formyl group, a $C_1$–$C_3$ alkylthio group, a dihydroxylboryl group, or a phenyl group which may optionally be substituted with a dihydroxyboryl group), a naphthyl group which may optionally be substituted with at least one substituent (e.g. a halogen atom, a $C_1$–$C_4$ alkyl group or a $C_1$–$C_3$ haloalkyl group), a thienyl group which may optionally be substituted with at least one substituent (e.g. a halogen atom or a $C_1$–$C_4$ alkyl group), a furyl group which may optionally be substituted with at least one substituent (e.g. a halogen atom or a $C_1$–$C_4$ alkyl group), a benzofuranyl group the benzene group of which may optionally be substituted with at least one substituent (e.g. a halogen atom, a $C_1$–$C_4$ alkyl group or a $C_1$–$C_3$ haloalkyl group), or $R^4$ and $R^5$ together form a ring;

a polymeric boric acid of the formula (5):

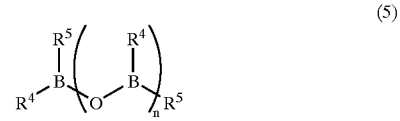

$$(5)$$

wherein $R^4$ and $R^5$ are the same as defined above, or $R^4$ and $R^5$ together form a ring, and n is an integer of at least 1; or a boroxine derivative of the formula (6):

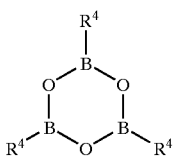

(6)

wherein R⁴ is the same as defined above; or mixtures thereof.

Examples of the $C_1$–$C_6$ alkoxy group for $R^4$, $R^5$ and $R^6$ in the formulae (4), (5) and (6) include a methoxy group, an ethoxy group, an isopropoxy group, a n-butoxy group, a tert.-butyl group, etc.

Examples of the $C_1$–$C_6$ alkyl group include a methyl group, an ethyl group, a n-propyl group, an isopropyl group, a n-butyl group, a sec.-butyl group, a tert.-butyl group, a n-pentyl group, a cyclopentyl group, a n-hexyl group, a cyclohexyl group, etc.

Examples of the phenyl group which may optionally be substituted include a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2,3-difluorophenyl group, a 3,4-difluorophenyl group, a 2,4-difluorophenyl group, a 2,5-difluorophenyl group, a 2,6-difluorophenyl group, a 3,5-difluorophenyl group, 2,3-dichlorophenyl group, a 3,4-dichlorophenyl group, a 2,4-dichlorophenyl group,;a 2,5-dichlorophenyl group, a 2,6-dichlorophenyl group, a 3,5-dichlorophenyl group, a 2,3-dibromophenyl group, a 3,4-dibromophenyl group, a 2,4-dibromophenyl group, a 2,5-dibromophenyl group, a 2,6-dibromophenyl group, a 3,5-dibromophenyl group, a 2-chloro-3-fluorophenyl group, a 3-chloro-2-fluorophenyl group, a 2-chloro-4-fluorophenyl group, a 4-chloro-2-fluorophenyl group, a 2-chloro-5-fluorophenyl group, a 5-chloro-2-fluorophenyl group, a 2-chloro-6-fluorophenyl group, a 3-chloro-4-fluorophenyl group, a 4-chloro-3-fluorophenyl group, a 3-chloro-5-fluorophenyl group, a 2-bromo-3-fluorophenyl group, a 3-bromo-2-fluorophenyl group, a 2-bromo-4-fluorophenyl group, a 4-bromo-2-fluorophenyl group, a 2-bromo-5-fluorophenyl group, a 5-bromo-2-fluorophenyl group, a 2-bromo-6-fluorophenyl group, a 3-bromo-4-fluorophenyl group, a 4-bromo-3-fluorophenyl group, a 3-bromo-5-fluorophenyl group, a 2-bromo-3-chlorophenyl group, a 3-bromo-2-chlorophenyl group, a 2-bromo-4-chlorophenyl group, a 4-bromo-2-chlorophenyl group, a 2-bromo-5-chlorophenyl group, a 5-bromo-2-chlorophenyl group, a 2-bromo-6-chlorophenyl group, a 3-bromo-4-chlorophenyl group, a 4-bromo-3-chlorophenyl group, a 3-bromo-5-chlorophenyl group, a 2,3,4-trifluorophenyl group, a 3,4,5-trifluorophenyl group, a 2,3,4-trichlorophenyl group, a 3,4,5-trichlorophenyl group, a 2,3,4-tribromophenyl group, a 3,4,5-tribromophenyl group, a 2-tolyl group, a 3-tolyl group, a 4-tolyl group, a 2-ethylphenyl group, a 3-ethylphenyl group, a 4-ethylphenyl group, a 2,3-xylyl group, a 3,4-xylyl group, a 2,4-xylyl group, a 2,5-xylyl group, a 2,6-xylyl group, a 3,5-xylyl group, a mesityl group, a 2-trifluoromethylphenyl group, a 3-trifluoromethylphenyl group, a 4-trifluoromethylphenyl group, a 3,5-bis (trifluoromethyl)phenyl group, a 2-anisyl group, a 3-anisyl group, a 4-anisyl group, a 2-nitrophenyl group, a 3-nitrophenyl group, a 4-nitrophenyl group, a 2-aminophenyl group, a 3-aminophenyl group, a 4-aminophenyl group, a 2-carboxyphenyl group, a 3-carboxyphenyl group, a 4-carboxyphenyl group, a 2-acetamidophenyl group, a 3-acetamidophenyl group, a 4-acetamidophenyl group, a 2-formylphenyl group, a 3-formylphenyl group, a 4-formylphenyl group, a 2-methylthiophenyl group, a 3-methylthiophenyl group, a 4-methylthiophenyl group, a 2-(dihydroxyboryl)phenyl group, a 3-(dihydroxyboryl)phenyl group, a 4-(dihydroxyboryl)phenyl group, a 2-biphenyl group, a 3-biphenyl group, a 4-biphenyl group, a 4-[4'-(dihydroxyboryl)phenyl]phenyl group, etc.

Examples of the naphthyl group which may optionally be substituted include a 1-naphthyl group, 2-naphthyl group, a 3-fluoro-1-naphthyl group, a 4-fluoro-1-naphthyl group, a 5-fluoro-1-naphthyl group, a 6-fluoro-1-naphthyl group, a 3-fluoro-2-naphthyl group, a 4-fluoro-2-naphthyl group, a 5-fluoro-2-naphthyl group, a 6-fluoro-2-naphthyl group, a 3-chloro-1-naphthyl group, a 4-chloro-1-naphthyl group, a 5-chloro-1-naphthyl group, a 6-chloro-1-naphthyl group, a 3-chloro-2-naphthyl group, a 4-chloro-2-naphthyl group, a 5-chloro-2-naphthyl group, a 6-chloro-2-naphthyl group, a 3-bromo-1-naphthyl group, a 4-bromo-1-naphthyl group, a 5-bromo-1-naphthyl group, a 6-bromo-1-naphthyl group, a 3-bromo-2-naphthyl group, a 4-bromo-2-naphthyl group, a 5-bromo-2-naphthyl group, a 6-bromo-2-naphthyl group, a 3-methyl-o-naphthyl group, a 4-methyl-1-naphthyl group, a 5-methyl-1-naphthyl group, a 6-methyl-1-naphthyl group, a 3-methyl-2-naphthyl group, a 4-methyl-2-naphthyl group, a 5-methyl-2-naphthyl group, a 4-methyl-2-naphthyl group, a 5-methyl-2-naphthyl group, a 6-methyl-2-naphthyl group, a 3-trifluoromethyl-1-naphthyl group, a 4-trifluoromethyl-1-naphthyl group, a 5-trifluoromethyl-1-naphthyl group, a 6-trifluoromethyl-1-naphthyl group, a 3-trifluoromethyl-2-naphthyl group, a 4-trifluoromethyl-2-naphthyl group, a 5-trifluoromethyl-2-naphthyl group, a 6-trifluoromethyl-2-naphthyl group, etc.

Examples of the thienyl group which may optionally be substituted include a 2-thienyl group, a 3-thienyl group, a 3-fluoro-2-thienyl group, a 4-fluoro-2-thienyl group, a 5-fluoro-2-thienyl group, a 2-fluoro-3-thienyl group, a 4-fluoro-3-thienyl group, a 5-fluoro-3-thienyl group, a 3-chloro-2-thienyl group, a 4-chloro-2-thienyl group, a 5-chloro-2-thienyl group, a 2-chloro-3-thienyl group, a 4-chloro-3-thienyl group, a 5-chloro-3-thienyl group, a 3-bromo-2-thienyl group, a 4-bromo-2-thienyl group, a 5-bromo-2-thienyl group, a 2-bromo-3-thienyl group, a 4-bromo-3-thienyl group, a 5-bromo-3-thienyl group, a 3-methyl-2-thienyl group, a 4-methyl-2-thienyl group, a 5-methyl-2-thienyl group, a 2-methyl-3-thienyl group, a 4-methyl-3-thienyl group, a 5-methyl-3-thienyl group, etc.

Examples of the furyl group which may optionally be substituted include a-2-furyl group, a 3-furyl group, a 3-fluoro-2-furyl group, a 4-fluoro-2-furyl group, a 5-fluoro-2-furyl group, a 2-fluoro-3-furyl group, a 4-fluoro-3-furyl group, a 5-fluoro-3-furyl group, a 3-chloro-2-furyl group, a 4-chloro-2-furyl group,-a 5-chloro-2-furyl group, a 2-chloro-3-furyl group, a 4-chloro-3-furyl group, a 5-chloro-3-furyl group, a 3-bromo-2-furyl group, a 4-bromo-2-furyl group, a 5-bromo-2-furyl group, a 2-bromo-3-furyl group, a 4-bromo-3-furyl group, a 5-bromo-3-furyl group, a 3-methyl-2-furyl group, a 4-methyl-2-furyl group, a 5-methyl-2-furyl group, a 2-methyl-3-furyl group, a 4-methyl-3-furyl group, a 2-methyl-3-furyl group, etc.

Examples of the benzofuranyl group which may optionally be substituted include a 2-benzofuranyl group, a 3-benzofuranyl group, a 4-fluoro-2-benzofuranyl group, a 5-fluoro-2-benzofuranyl group, a 6-fluoro-2-benzofuranyl group, a 7-fluoro-2-benzofuranyl group, a 4-fluoro-3- benzofuranyl group, a 5-fluoro-3-benzofuranyl group, a 6-fluoro-3-benzofuranyl group, a 7-fluoro-3-benzofuranyl group, a 4-chloro-2-benzofuranyl group, a 5-chloro-2-benzofuranyl group, a 6-chloro-2-benzofuranyl group, a 7-chloro-2-benzofuranyl group, a 4-chloro-3-benzofuranyl group, a 5-chloro-3-benzofuranyl group, a 6-chloro-3-benzofuranyl group, a 7-chloro-3-benzofuranyl group, a 4-bromo-2-benzofuranyl group, a 5-bromo-2-benzofuranyl group, a 6-bromo-2-benzofuranyl group, a 7-bromo-2-benzofuranyl group, a 4-bromo-3-benzofuranyl group, a 5-bromo-3-benzofuranyl group, a 6-bromo-3-benzofuranyl group, a 7-bromo-3-benzofuranyl group, a 4-methyl-2-benzofuranyl group, a 5-methyl-2-benzofuranyl group, a 6-methyl-2-benzofuranyl group, a 7-methyl-2-benzofuranyl group, a 4-methyl-3-benzofuranyl group, a 5-methyl-3-benzofuranyl group, a 6-methyl-3-benzofuranyl group, a 7-methyl-3-benzofuranyl group, a 4-trifluoromethyl-2-benzofuranyl group, a 5-trifluoromethyl-2-benzofuranyl group, a 6-trifluoromethyl-2-benzofuranyl group, a 7-trifluoromethyl-2-benzofuranyl group, a 4-trifluoromethyl-3-benzofuranyl group, a 5-trifluoromethyl-3-benzofuranyl group, a 6-trifluoromethyl-3-benzofuranyl group, a 7-trifluoromethyl-3-benzofuranyl group, etc.

Examples of the combined group of $R^4$ and $R^5$ which form a ring include a $C_4$–$C_5$ alkylene group which may be substituted with at least one methyl group such as a 1,4-tetramethylene group, or a 1,5-pentamethylene group, and a $C_2$–$C_4$ alkylenedioxy group !which may be substituted with at least one methyl group such as a 1,2-ethylenedioxy group, a 1,2-(1,1,2,2-tetramethyl)ethylene-dioxy group or a 1,3-tetramethylenedioxy group, and a 1,2-phenylenedioxy group, etc.

Examples of the borane compound of the formula (4) include boric acid derivatives (e.g. methylboric acid, ethylboric acid, isopropylboric acid, n-butylboric acid, n-pentylboric acid, cyclopentylboric acid, n-hexylboric acid, cyclohexylboric acid, phenylboric acid, 2-flutiorophenylboric acid, 3-fluorophenylboric acid, 4-fluorophenylboric acid, 2-chlorophenylboric acid, 3-chlorophenylboric acid, 4-chlorophenylboric acid, 2-bromo-phenylboric acid, 3-bromophenylboric acid, 4-bromophenylboric acid, 3,5-difluorophenylboric acid, 2,3-dichlorophenylboric acid, 3,4-dichlorophenylboric acid, 2,4-dichlorophenylboric acid, 3, 5-dichlorophenylboric acid, 3, 5-dibromophenylboric acid, 3-chloro-4-fluorophenylboric acid, 3,4,5-trifluorophenylboric acid, 3,4,5-trichlorophenylboric acid, 3,4,5-tribromophenyl-boric acid, 2,3,4,5,6-pentafluorophenylboric acid, 2-tolylboric acid, 3-tolylboric acid, 4-tolylboric acid, 4-ethylphenylboric acid, 3,4-xylylboric acid, mesitylboric acid, 2-trifluoromethylphenylboric acid, 3-trifluoromethylphenylboric acid, 4-trifluoromethylphenylboric acid, 3,5-bis(trifluoromethyl)phenylboric acid, 2-anisylboric acid, 3-anisylboric acid, 4-anisylboric acid, 3-nitrophenylboric acid, 4-nitrophenylboric acid, 3-aminophenylboric acid, 2-carboxyphenylboric acid, 4-carboxyphenylboric acid, 3-acetamidophenylboric acid, 2-formylphenylboric acid, 3-formylphenylboric acid, 4-formylphenylboric acid, 2-methylthiophenylboric acid, 4-methylthiophenylboric acid, 4-biphenylboric acid, 1,2-phenylenediboric acid, 1,3-phenylenediboric acid, 1,4-phenylenediboric acid, 4,4'-biphenyleneboric acid, 1-naphthylboric acid, 2-naphthylboric acid, 2-thienylboric acid, 3-thienylboric acid, 5-chloro-2-thienylboric acid, 2-furylboric acid, 3-furylboric acid, 2-benzofuranylboric acid, 3-benzofuranylboric acid, etc.);

borinic acid derivatives (e.g. dimethylborinic acid, diethylborinic acid, diphenylborinic acid, bis(3,4,5-trifluorophenyl)borinic acid, bis(2,3,4,5,6-pentafluorophenyl) borinic acid, bis (4-methylphenyl) borinic acid, bis[3,5-bis(trifluoromethyl)-phenyl] borinic acid, etc.);

trimethylborane, triethylborane, triphenylborane, tris(3,4,5-trifluorophenyl)borane, tris(2,3,4,5,6-pentafluorophenyl)borane, tris(4-methylphenyl)borane, tris[3,5-bis(trifluorqmethyl)phenyl]borane, tris(3-nitrophenyl)borane, dimethoxyphenylborane, 2-phenyl-1,3,2-dioxabororane, 2-phenyl-4,4,5,5-tetramethyl-1,3,2-dioxabororane, dimethdxy-(4-methylphenyl)borane, 2-(4-methyl)phenyl-1,3,2-dioxabororane, 2-(4-methyl)phenyl-4,4,5,5-tetramethyl-1,3,2-dioxabororane, dimethoxy-(3,4,5-trifluorophenyl)borane, 2-(3,4,5-trifluoro)phenyl-1,3,2-dioxabororane, 2-(3,4,5-trifluoro)phenyl-4,4,5,5-tetramethyl-1,3,2-dioxabororane, dimethoxy-(2,3,4,5,6-pentafluorophenyl)borane, 2-(2,3,4,5,6-pentafluoro)phenyl-1,3,2-dioxabororane, 2-(2,3,4,5,6-pentafluoro)phenyl-4,4,5,5-tetramethyl-1,3,2-dioxabororane, dimethoxy-(3,5-bistrifluoro-methyl)phenylborane, 2-(3,5-bistrifluoromethyl)phenyl-1,3,2-dioxabororane, 2-(3,5-bistrifluoromethyl)phenyl-4,4,5,5-tetramethyl-1,3,2-dioxabororane, dimethoxy-(3-nitrophenyl)-borane, 2-(3-nitro)phenyl-1,3,2-dioxabororane, 2-(3-nitro)phenyl-4,4,5,5-tetramethyl-1,3,2-dioxabororane, etc.

In a polymeric boric acid of the formula (5), n is an integer of 1 or more, and preferably from 1 to 5.

Examples of the polymeric boric acid of the formula (5) include boric acid derivatives or borinic acid derivative, and their anhydrides among the above borane compounds of the formula (4).

Examples of thelboroxine derivative of the formula (6) include trimethylboroxine, triethylboroxine, triphenylboroxine, tris(3,4,5-trifluorophneyl)boroxine, tris (2,3,4,5,6-pentafluorophenyl)boroxine, tris(4-methylphenyl)boroxine, tris[3,5-bis(trifluoromethyl)phenyl]boroxine, tris(3-nitrophenyl)boroxine, etc.

Preferred examples of the borane compound (4), the polymeric boric acid (5) or the boroxine derivative (6) include methylboric acid, n-butylboric acid, phenylboric acid, 3-fluorophenylboric acid, 4-fluorophenylboric acid, 4-chlorophenylboric acid, 4-bromophenylboric acid, 3,5-dichlorophenylboric acid, 3-chloro-4-fluorophenylboric acid, 4-tolylboric acid, 3-trifluoromethylphenylboric acid, 4-trifluoromethylphenylboric acid, 3,5-bis(trifluoromethyl)phenylboric acid, 3-anisylboric acid, 3-nitrophenylboric acid; 4-carboxyphenylboric acid, 3-acetamidophenylboric acid, 3-formylphenylboric acid, 4-formylphenylboric acid, 4-methylthiophenylboric acid, 2-naphthylboric acid, 1,4-phenylenediboric acid, diphenylborinic acid, bis(4-methylphenyl)borinic acid, and their polymeric derivatives (anhydrides); triphenylborane, tris(4-methylphenyl)borane, triphenylboroxine, tris(4-methylphenyl)boroxine, and the like. Particularly preferred compounds are phenylboric acid, 4-tolylboric acid and their anhydrides; triphenylboroxine and tris(4-methyl)phenylboroxine.

Among the borane compounds of the formula (4), borinic acid derivatives in which one of $R^4$, $R^5$ and $R_6$ is a hydroxyl group, or boric acid derivatives in which two of $R^4$, $R^5$ and $R_6$ are hydroxyl groups may also form polymeric derivatives (anhydrides) represented by the formula (5) or (6). In the present invention, monomeric compounds, polymeric compounds and their mixtures can be used.

Now, a nitrogen-containing aromatic compound used in the process of the present invention is explained.

A nitrogen-containing aromatic compound used in the process of the present invention is usually pyridine, quinoline or isoquinoline, which may optionally be substituted with at least one substituent is selected from a halogen atom (e.g. a fluorine atom, a chlorine atom, a bromine atom and an iodine atom), a $C_1$–$C_3$ alkyl group (e.g. a methyl group, an ethyl group, a propyl group, an isopropyl group, etc.) and a di-($C_1$–$C_3$ alkyl)amino group.

Specific examples of such a nitrogen-containing aromatic compound include pyridine, quinoline, isoquinoline, 4-dimethylaminopyridine, 2-picoline, 3-picoline, 4-picoline, 2,3-lutidine, 2,4-lutidine, 2,5-lutidine, 2,6-lutidine, 3,4-lutidine, 3,5-lutidine, 3-chloropyridine, 2-ethyl-3-methylpyridine, 5-ethyl-2-methylpyridine, etc.

Preferred nitrogen-containing aromatic compounds are pyridines which may be substituted with at least one alkyl group, in particular, at least one $C_1$–$C_3$ alkyl group, for example, 2-picoline, 2,3-lutidine, 2,4-lutidine, 2,5-lutidine, 2,6-lutidine, 2-ethyl-3-methylpyridine, 5-ethyl-2-methylpyridine,etc. Among them, pyridines having a substituent at the 2-position, for example, 5-ethyl-2-methylpyridine are particularly preferred.

The combination of a boron compound and a nitrogen-containing aromatic compound can be the combination of the above exemplified compounds. In particular, the combination of phenylboric acid and 5-ethyl-2-methylpyridine, the combination of 4-tolylboric acid and 5-ethyl-2-methylpyridine, the combination of triphenylboroxine and 5-ethyl-2-methylpyridine, and the combination of tris(4-methylphenyl)boroxine and 5-ethyl-2-methylpyridine are preferred from the viewpoint of overall properties.

The process of the present invention is usually carried out in a solvent. A reaction temperature is usually in the range between about 50° C. and about 250° C., preferably in the range between about 100° C. and about 200° C. A reaction time is usually from split second to about 48 hours, preferably from 1 to 24 hours.

Examples of a solvent which may be used in the process of the present invention:include aliphatic hydrocarbons (e.g. heptane, octane, ligroin, etc.), aromatic hydrocarbons (e.g. benzene, toluene, ethylbenzene, xylene, mesitylene, etc.), halogeneated hydrocarbons (e.g. 1,2-dichloroethane, chlorobenzene, dichlorobenzene, trichlorobenzene, etc.), ethers (e.g. 1,4-dioxane, ethylene glycol dimethyl ether, methyl tert.-butyl ether, etc.), ketones (e.g. methyl isobutyl ketone, cyclohexanone, etc.), acid amides (e.g. N,N-dimethylformamide, etc.), alcohols (e.g. propanol, butanol, amyl alcohol, ethylene glycol, diethylene glycol, etc.), and their mixtures.

The amount of a nitrogen-containing compound is usually from 0.01 to a solvent amount, preferably from 0.1 to 20 moles, per 1 mole of a carboxylic acid derivative of the formula (2).

The amount of a boron compound is usually from 0.0001 to 5 moles, preferably from 0.001 to 3 moles, in terms of a boron atom, per 1 mole of a carboxylic acid derivative of the formula (2).

The carboxylic acid of the formula (2) is a known compound from WO98/17632, or can be prepared by the method described in this WO publication.

The carboxylic acid of the formula (2) or its salt has geometric isomers due to the presence of a double bond, optical isomers due to the presence of an asymmetric carbon atom and diastereomers. Any one of such isomers or a mixture thereof may be used in the process of the present invention.

In the process of the present invention, the raw material, a solvent and the like can be charged at once, although it is possible to charge a carboxylic acid derivative of the formula (2), a nitrogen-containing compound and the like by several portions to carry out the reaction.

After the completion of the reaction, the reaction mixture is post-treated, for example, the reaction mixture as such is concentrated, or it is washed with an aqueous solution of an inorganic acid such as hydrochloric acid, sulfuric acid, etc. and the organic layer is dried and concentrated. If necessary, the concentrated product may be purified by recrystallization or with column chromatography to recover a pyridazin-3-on of the formula (1).

In the process of the present invention, the reaction may be carried out with azeotropic dehydration and/or in the presence of a dehydrator. Examples of such a dehydrator include zeolites such as molecular sieves, silica gel, magnesium sulfate, sodium sulfate, calcium sulfate, copper sulfate, etc. Preferably zeolites such as molecular sieves, in particular, Molecular Sieve 3A, are used.

When a solid dehydrator is used, it is removed by filtration from a reaction mixture, and then the reaction mixture is subjected to the above post-treatment to recover a pyridazin-3-one of the formula (1).

Preferred but unlimiting examples of pyridazin-3-on derivatives of the formula (1) are as follows:

| Compound No. | Pyridazin-3-on derivatives of the formula (1) Pyridazine-3-on derivative |
|---|---|
| 1-1 | (structure: 4-chlorophenyl-N-N=pyridazinone with CH₃ and CF₃) |
| 1-2 | (structure: 3-chloro-6-fluoro-4-hydroxyphenyl pyridazinone with CH₃ and CF₃) |
| 1-3 | (structure: 3-chloro-6-fluoro-4-isopropoxyphenyl pyridazinone with CH₃ and CF₃) |
| 1-4 | (structure: 3-chloro-6-fluoro-4-methoxyphenyl pyridazinone with CH₃ and CF₃) |

-continued

Pyridazin-3-on derviatives of the formula (1)

| Compound No. | Pyridazine-3-on derivative |
|---|---|
| 1-5 | 2-(4-chloro-2-fluoro-5-ethoxycarbonyloxyphenyl)-4-methyl-5-trifluoromethyl-pyridazin-3(2H)-one |
| 1-6 | 2-(4-chloro-2-fluoro-5-carboxymethoxyphenyl)-4-methyl-5-trifluoromethyl-pyridazin-3(2H)-one |
| 1-7 | 2-(4-chloro-2-fluoro-5-isopropoxyphenyl)-4-ethyl-5-trifluoromethyl-pyridazin-3(2H)-one |
| 1-8 | 2-(4-chloro-2-fluoro-5-methoxyphenyl)-4-ethyl-5-trifluoromethyl-pyridazin-3(2H)-one |
| 1-9 | 2-(4-chloro-2-fluoro-5-ethoxyphenyl)-4-ethyl-5-trifluoromethyl-pyridazin-3(2H)-one |
| 1-10 | 2-(4-chloro-2-fluoro-5-propargyloxyphenyl)-4-methyl-5-trifluoromethyl-pyridazin-3(2H)-one |
| 1-11 | 2-(4-chloro-2-fluoro-5-propargylthiophenyl)-4-methyl-5-trifluoromethyl-pyridazin-3(2H)-one |
| 1-12 | 2-(2,4-dichloro-5-isopropoxyphenyl)-5-trifluoromethyl-pyridazin-3(2H)-one |
| 1-13 | 2-(2,4-dichloro-5-methoxyphenyl)-5-trifluoromethyl-pyridazin-3(2H)-one |
| 1-14 | 2-(2,4-dichloro-5-ethoxyphenyl)-5-trifluoromethyl-pyridazin-3(2H)-one |
| 1-15 | 2-(2,4-dichloro-5-isopropoxyphenyl)-4-ethyl-5-trifluoromethyl-pyridazin-3(2H)-one |
| 1-16 | 2-(2,4-dichloro-5-methoxyphenyl)-4-ethyl-5-trifluoromethyl-pyridazin-3(2H)-one |
| 1-17 | 2-(2,4-dichloro-5-ethoxyphenyl)-4-ethyl-5-trifluoromethyl-pyridazin-3(2H)-one |
| 1-18 | 2-(4-chlorophenyl)-5-trifluoromethyl-pyridazin-3(2H)-one |

EFFECTS OF THE INVENTION

According to the present invention, pyridazin-3-on derivatives having good herbicidal activities can be obtained at a high yield and high purity.

EXAMPLES

The present invention will be illustrated by the following examples, which do not limit the scope of the invention in any way.

Example 1

3-Carboxy-2-trifluoromethyl-2-hydroxy-1-butanal-1-(4-chloro-2-fluoro-5-hydroxyphenylhydrazone) (Compound 2–2) (5.62 g), phenylboric acid (0.38 g), Molecular Sieve 4A (powder) (2.70 g), toluene (16.14 g) and 5-ethyl-2-methylpyridine (2.82 g) were charged in a reactor, and stirred at a temperature between 110° C. and 115° C. for 10 hours. After the reaction mixture was cooled to room temperature, methanol (10.0 g) was added to the mixture, and the supernatant was analyzed with LC by an internal standard method, which is explained below. The yield of 2-(2-fluoro-4-chloro-5-hydroxyphenyl)-4-methyl-5-trifluoromethylpyridazin-3-on (Compound 1–2) was 91.2%.

Internal Standard Method

Solutions containing a beforehand isolated objective compound and a standard compound, which is used as the standard of a peak area, in various compositions are prepared, and detected intensities of those solutions are measured by liquid chromatography analysis. Then, a calibration curve is drawn from the weight ratios and the peak area ratios of the objective compound to the standard compound.

Thereafter, the precise amount of the standard compound is added to the specific amount of a reaction mixture after the completion of a reaction, and the mixture is analyzed by liquid chromatography. The concentration of the objective compound is calculated using the calibration curve from the obtained peak area ratio of the objective compound to the standard compound.

In the examples, ethoxybenzene was used as a standard compound.

Examples 2 to 21

The same procedures as those in Example 1 were repeated except that a boric acid derivative shown in Table 1 was used in place of phenylboric acid (0.38 g). Then, the supernatant of the reaction mixture was analyzed by the internal standard method. The yield of 2-(2-fluoro-4-chloro-5-hydroxyphenyl)-thyl-5-trifluoromethylpyridazin-3-on is shown in Table 1.

TABLE 1

| Ex. No. | Boric acid derivative | Amount (g) | Yield (%) |
| --- | --- | --- | --- |
| 2 | n-Butylboric acid | 0.33 | 88.3 |
| 3 | 4-Tolylboric acid | 0.41 | 89.8 |
| 4 | 3-Fluorophenylboric acid | 0.42 | 90.0 |
| 5 | 4-Fluorophenylboric acid | 0.42 | 87.4 |
| 6 | 3-Formylphenylboric acid | 0.45 | 86.8 |
| 7 | 4-Formylphenylboric acid | 0.45 | 87.9 |
| 8 | 3-Anisylphenylboric acid | 0.46 | 89.2 |
| 9 | 4-Chlorophenylboric acid | 0.47 | 92.2 |
| 10 | 4-Carboxyphenylboric acid | 0.50 | 87.7 |
| 11 | 3-Nitrophenylboric acid | 0.50 | 86.1 |
| 12 | 4-Methylthiophenylboric acid | 0.50 | 88.7 |
| 13 | 2-Naphthylboric acid | 0.52 | 91.8 |
| 14 | 3-Chloro-4-fluorophenylboric acid | 0.52 | 88.9 |
| 15 | 3-Acetamidophenylboric acid | 0.67 | 91.9 |
| 16 | 3-(Trifluoromethyl)phenylboric acid | 0.57 | 86.5 |
| 17 | 4-(Trifluoromethyl)phenylboric acid | 0.58 | 85.1 |

TABLE 1-continued

| Ex. No. | Boric acid derivative | Amount (g) | Yield (%) |
| --- | --- | --- | --- |
| 18 | 3,5-Dichlorophenylboric acid | 0.57 | 87.6 |
| 19 | 4-Bromophenylboric acid | 0.60 | 86.5 |
| 20 | 3,5-Bis(trifluoromethyl)phenylboric acid | 0.77 | 89.8 |
| 21 | 1,4-Phenylenediboric acid | 0.50 | 92.7 |

Example 22

The same procedures as those in Example 11 were repeated except that 0.75 g of 3-nitrophenylboric acid and 3.76 g of 5-ethyl-2-methylpyridine were used. Then, the supernatant of the reaction mixture was analyzed by the internal standard method. The yield of 2-(2-fluoro-4-chloro-5-hydroxyphenyl)-4-methyl-5-trifluoromethylpyridazin-3-on was 91.6%.

Example 23

3-Carboxy-2-trifluoromethyl-2-hydroxy-1-butanal-1-(4-chloro-2-fluoro-5-hydroxyphenylhydrazone) (9.43 g), phenylboric acid (0.31 g), Molecular Sieve 3A (powder) (8.97 g), toluene (44.72 g) and 5-ethyl-2-methylpyridine (4.69 g) were charged in a reactor, and stirred at 114° C. for 7 hours. After the reaction mixture was cooled to room temperature, the molecular sieve was removed by filtration, and the filtrate was analyzed with LC by an: internal standard method. The yield of 2-(2-fluoro-4-chloro-5-hydroxyphenyl)-4-methyl-5-trifluoromethylpyridazin-3-on was 93.5%.

Example 24

The same procedures as those in Example 23 were repeated except that 0.61 g of phenylboric acid and 18.83 g of 5-ethyl-2-methylpyridine were used. Then, the filtrate was analyzed with LC by the internal standard method. The yield of 2-(2-fluoro-4-chloro-5-hydroxyphenyl)-4-methyl-5-trifluoromethylpyridazin-3-on was 98.2%.

Example 25

3-Carboxy-2-trifluoromethyl-2-hydroxy-1-butanal-1-(4-chloro-2-fluoro-5-hydroxyphenylhydrazone) (4.62 g), phenylboric acid (0.55 g), Molecular Sieve 4A (powder) (8.09 g), toluene (80.69 g) and 5-ethyl-2-methylpyridine (2.83 g) were charged in a reactor, and stirred at a temperature between 109° C. and 112° C. for 3 hours. Then, 3-carboxy-2-trifluoromethyl-2-hydroxy-1-butanal-1-(4-chloro-2-fluoro-5-hydroxyphenylhydrazone) (4.61 g) and 5-ethyl-2-methylpyridine (1.84 g) were charged. After further 3 hours, 3-carboxy-2-trifluoromethyl-2-hydroxy-1-butanal-1-(4-chloro-2-fluoro-5-hydroxyphenylhydrazone) (4.59 g) and 5-ethyl-2-methylpyridine (1.88 g) were charged. After another 3 hours, 3-carboxy-2-trifluoromethyl-2-hydroxy-1-butanal-1-(4-chloro-2-fluoro-5-hydroxyphenylhydrazone) (4.61 g) and 5-ethyl-2-methylpyridine (1.85 g) were charged, and the mixture was heated at the same temperature as above for 11 hours.

After the reaction mixture was cooled to room temperature, the molecular sieve was removed by filtration, and the filtrate was analyzed with LC by an internal standard method. The yield of 2-(2-fluoro-4-chloro-5-hydroxyphenyl)-4-methyl-5-trifluoromethylpyridazin-3-on was 88.0%.

Example 26

The same procedures as those in Example 25 were repeated except that formed water was azeotropically removed. The filtrate was analyzed with LC by an internal standard method. The yield of 2-(2-fluoro-4-chloro-5-hydroxyphenyl)-4-methyl-5-trifluoromethylpyridazin-3-on was 92.1%.

Example 27

The same procedures as those in Example 26 were repeated except that monochlorobenzene (80.76 g) was used in place of toluene. The filtrate was analyzed with LC by an internal standard method. The yield of 2-(2-fluoro-4-chloro-5-hydroxyphenyl)-4-methyl-5-trifluoromethylpyridazin-3-on was 93.7%.

Example 28

3-Carboxy-2-trifluoromethyl-2-hydroxy-1-butanal-1-(4-chloro-2-fluoro-5-hydroxyphenylhydrazone) (5.65 g), phenylboric acid (0.73 g), Molecular Sieve 3A (powder) (21.52 g), toluene (107.41 g) and 5-ethyl-2-methylpyridine (3.75 g) were charged in a reactor, and stirred at a temperature between 113° C. and 115° C. for 3 hours. Then, 3-carboxy-2-trifluoromethyl-2-hydroxy-1-butanal-1-(4-chloro-2-fluoro-5-hydroxyphenylhydrazone) (5.63 g) and 5-ethyl-2-methylpyridine (2.51 g) were charged. After further 3 hours, 3-carboxy-2-trifluoromethyl-2-hydroxy-1-butanal-1-(4-chloro-2-fluoro-5-hydroxyphenylhydrazone) (5.63 g) and 5-ethyl-2-methylpyridine (2.50 g) were charged. After another 3 hours, 3-carboxy-2-trifluoromethyl-2-hydroxy-1-butanal-1-(4-chloro-2-fluoro-5-hydroxyphenylhydrazone) (5.66 g) and 5-ethyl-2-methylpyridine (2.49 g) were charged, and the mixture was heated at the same temperature as above for 6 hours.

After the reaction mixture was cooled to room temperature, the molecular sieve was removed by filtration, and the filtrate was analyzed with LC by an internal standard method. The yield of 2-(2-fluoro-4-chloro-5-hydroxyphenyl)-4-methyl-5-trifluoromethylpyridazin-3-on 99.3%.

Example 29

The same procedures as those in Example 23 were repeated except that 2,6-lutidine (8.10 g) was used in place of 5-ethyl-2-methylpyridine (4.69 g), and the mixture was stirred at a temperature between 115° C. and 116° C. for 15 hours. The filtrate was analyzed with LC by an internal standard method. The yield of 2-(2-fluoro-4-chloro-5-hydroxyphenyl)-4-methyl-5-trifluoromethylpyridazin-3-on was 90.9%.

Example 30

3-Carboxy-2-trifluoromethyl-2-hydroxy-1-butanal-1-(4-chloro-2-fluoro-5-hydroxyphenylhydrazone) (16.68 g), phenylboric acid (0.55 g), Molecular Sieve 3A (powder) (16.24 g), toluene (80.83 g) and 2-picolin (12.61 g) were charged in a reactor, and stirred at a temperature between 114 and 115° C. for 7 hours. After the reaction mixture was cooled to room temperature, the molecular sieve was removed by filtration, and the filtrate was analyzed with LC by an internal standard method. The yield of 2-(2-fluoro-4-chloro-5-hydroxyphenyl)-4-methyl-5-trifluoromethylpyridazin-3-on was 91.0%.

Example 31

3-Carboxy-2-trifluoromethyl-2-hydroxy-1-butanal-1-(4-chloro-2-fluoro-5-hydroxyphenylhydrazone) (16.48 g), triphenylboroxine (0.48 g), Molecular Sieve 3A (powder) (16.37 g), toluene (84.91 g) and 5-ethyl-2-methylpyridine (17.06 g) were charged in a reactor, and stirred at a temperature between 114 and 115° C. for 6 hours. After the reaction mixture was cooled to room temperature, the molecular sieve was removed by filtration, and the filtrate was analyzed with LC by an internal standard method. The yield of 2-(2-fluoro-4-chloro-5-hydroxyphenyl)-4-methyl-5-trifluoromethylpyridazin-3-on was 93.6%.

Example 32

The same procedures as those in Example 31 were repeated except that diphenylborinic acid (0.81 g) was used in place of triphenylboroxine (0.48 g). After the reaction mixture was cooled to room temperature, the molecular sieve was removed by filtration, and the filtrate was analyzed with LC by an internal standard method. The yield of 2-(2-fluoro-4-chloro-5-hydroxyphenyl)-4-methyl-5-trifluoromethylpyridazin-3-on was 93.4%.

Example 33

The same procedures as those in Example 31 were repeated except that triphenylborane (1.14 g) was used in place of triphenylboroxine (0.48 g). After the reaction mixture was cooled to room temperature, the molecular sieve was removed by filtration, and the filtrate was analyzed with LC by an internal standard method. The yield of 2-(2-fluoro-4-chloro-5-hydroxyphenyl)-4-methyl-5-trifluoromethylpyridazin-3-on was 95.4%.

Reference Example 1

3-Carboxy-2-trifluoromethyl-2-hydroxy-1-butanal-1-(4-chloro-2-fluoro-5-hydroxyphenylhydrazone) (0.315 g) was dissolved in the mixture of acetic acid (1.0 ml) and pyridine (1.0 ml) under a nitrogen atmosphere, and stirred at 120° C. for 8 hours. After the reaction mixture was cooled to room temperature, it was concentrated under reduced pressure, and the residue was diluted with diethyl ether (100 ml). Then, the diluted solution was washed with 3N hydrochloric acid (each 20 ml) twice, and saturated sodium bicarbonate (30 ml) once, dried over magnesium sulfate, filtrated and concentrated under reduced pressure. The residue was subjected to column chromatography. Thus, 2-(2-fluoro-4-chloro-5-hydroxyphenyl)-4-methyl-5-trifluoromethylpyridazin-3-on (0.227 g) was obtained.

What is claimed is:

1. A method for preparing a pyridazin-3-on derivative of the formula (1):

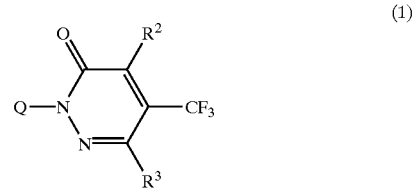

(1)

wherein $R^2$ is a hydrogen atom or a $C_1$–$C_3$ alkyl group, $R^3$ is a hydrogen atom or a $C_1$–$C_3$ alkyl group, and Q is an optionally substituted phenyl group of the formula (3):

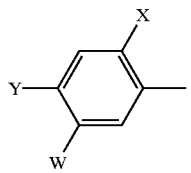

(3)

wherein X is a hydrogen atom or a halogen atom, Y is a halogen atom, and W is a hydrogen atom or a group of the formula: —$ZR^1$ in which Z is an oxygen atom or a sulfur atom, and $R^1$ is a hydrogen atom, a $C_1$–$C_6$ alkyl group, a $C_1$–$C_6$ haloalkyl group, a $C_3$–$C_8$ cycloalkyl group, a benzyl group, a $C_3$–$C_6$ alkenyl group, a $C_3$–$C_6$ haloalkenyl group, a $C_3$–$C_6$ alkynyl group, a $C_3$–$C_6$ haloalkynyl group, a cyano-$C_1$–$C_6$ alkyl group, a $C_2$–$C_8$ (alkoxyalkyl) group, a $C_2$–$C_8$ (alkoxythioalkyl) group, a carboxy-$C_1$–$C_6$ alkyl group, ($C_1$–$C_8$ alkoxy)carbonyl-$C_1$–$C_6$ alkyl group, a [($C_1$–$C_4$ alkoxy)-$C_1$–$C_4$ alkoxy]carbonyl-$C_1$–$C_6$ alkyl group, a ($C_3$–$C_8$ cycloalkoxy)carbonyl-$C_1$–$C_6$ alkyl group or a [($C_1$–$C_6$ alkoxy)carbonyl-$C_1$–$C_6$ alkyl]oxycarbonyl-$C_1$–$C_6$ alkyl; comprising the step of ring closing a carboxylic acid derivative of the formula (2):

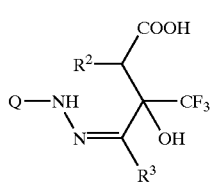

(2)

wherein $R^2$, $R^3$ and Q are the same as defined above, or its salt in the presence of a nitrogen-containing aromatic compound and at least one boron compound selected from formula (4), (5) and (6);

a borane compound of the formula (4):

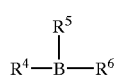

(4)

wherein $R^4$, $R^5$ and $R^6$ are the same or different and represent a hydroxyl group, a $C_1$–$C_6$ alkyl group, a $C_1$–$C_6$ alkoxy group, a phenyl group which may optionally be substituted with at least one substituent selected from a halogen atom, a $C_1$–$C_4$ alkyl group, a $C_1$–$C_3$ haloalkyl group, a $C_1$–$C_3$ alkoxy group, a nitro group, an amino group, a carboxyl group, a $C_1$–$C_3$ amide group, a formyl group, a $C_1$–$C_3$ alkylthio group, a dihydroxylboryl group and a phenyl group that may optionally be substituted with a dihydroxyboryl group, a naphthyl group which may optionally be substituted with at least one substituent selected from a halogen atom, a $C_1$–$C_4$ alkyl group and a $C_1$–$C_3$ haloalkyl group, a thienyl group which may optionally be substituted with at least one substituent selected from a halogen atom and a $C_1$–$C_4$ alkyl group, a furyl group which may optionally be substituted with at least one substituent selected from a halogen atom and a $C_1$–$C_4$ alkyl group, a benzofuranyl group. the benzene group of which may optionally be substituted with at least one substituent selected from a halogen atom, a $C_1$–$C_4$ alkyl group and a $C_1$–$C_3$ haloalkyl group, or $R^4$ and $R^5$ together form a ring;

a polymeric boric acid of the formula (5):

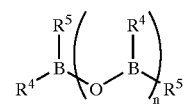

(5)

wherein $R^4$ and $R^5$ are the same as defined above, or $R^4$ and $R^5$ together form a ring, and n is an integer of at least 1; and a boroxine derivative of the formula (6):

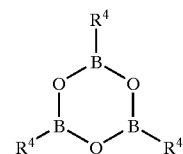

(6)

wherein $R^4$ is the same as defined above.

2. A process according to claim 1, wherein Z in the formula (3) is an oxygen atom.

3. A process according to claim 1, wherein W in the formula (3) is a hydroxyl group.

4. A process according to claim 1, wherein X in the formula (3) is a fluorine atom.

5. A process according to claim 1, wherein X and Y in the formula (3) are a fluorine atom and a chlorine atom, respectively.

6. A process according to claim 1, wherein $R^2$ and $R^3$ in the formulae (1) and (2) independently represent a hydrogen atom or a methyl group.

7. A process according to claim 1, wherein $R^2$ and $R^3$ in the formulae (1) and (2) are a methyl group and a hydrogen atom, respectively.

8. A process according to claim 1, wherein said nitrogen-containing aromatic compound is pyridine which may option ally be substituted with at least one alkyl group.

9. A process according to claim 1, wherein said nitrogen-containing aromatic compound is 5-ethyl-2-methylpyridine.

10. A process according to claim 1, wherein said borane compound of the formula (4) is phenylboric acid or 4-tolylboric acid.

11. A process according to claim 1, wherein said boroxine derivative of the formula (6) is triphenylboroxine or tris (4-methylphenyl) boroxine.

12. A process according to claim 1, wherein said nitrogen-containing compound is 5-ethyl-2-methylpyridine, and said borane compound of the formula (4) is phenylboric acid.

13. A process according to claim 1, wherein said nitrogen-containing compound is 5-ethyl-2-methylpyridine, and said boroxine derivative of the formula (6) is triphenylboroxine.

14. A process according to claim 1, wherein said boron compound is used in an amount of from 0.001 to 3 moles, in terms of a boron atom, per 1 mole of said carboxylic acid derivative of the formula (2) or its salt.

15. A process according to claim 1, wherein the reaction is carried out with azeotropic dehydration and/or in the presence of a dehydrator.

16. A process according to claim 15, wherein said dehydrator is a molecular sieve.

17. A process according to claim 15, wherein said molecular sieve is Molecular Sieve 3A.

18. A process according to claim 1, wherein the reaction is carried out at a temperature of from 100° C. to 200° C.

* * * * *

UNITED STATES PATENT AND TRADEMARK OFFICE
CERTIFICATE OF CORRECTION

PATENT NO.    : 6,500,951 B1
DATED         : December 31, 2002
INVENTOR(S)   : Yanagawa et al.

It is certified that error appears in the above-identified patent and that said Letters Patent is hereby corrected as shown below:

<u>Column 20,</u>
Line 63, please change "claim 15" to -- claim 16 --

Signed and Sealed this

Sixteenth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,500,951 B1                                                         Page 1 of 1
DATED          : December 31, 2002
INVENTOR(S)    : Yanagawa et al.

It is certified that error appears in the above-identified patent and that said Letters Patent is hereby corrected as shown below:

Title page,
Item [86], PCT Date, please change: "Jun. 20, 2001" to -- Jun. 28, 2001 --

Signed and Sealed this

Eleventh Day of November, 2003

JAMES E. ROGAN
*Director of the United States Patent and Trademark Office*